(12) United States Patent
Parks

(10) Patent No.: US 7,093,480 B2
(45) Date of Patent: Aug. 22, 2006

(54) METHOD AND APPARATUS TO STRESS TEST MEDICAMENT INHALATION AEROSOL DEVICE BY INDUCTIVE HEATING

(75) Inventor: Kevin Ray Parks, Durham, NC (US)

(73) Assignee: Smithkline Beecham Corporation, Philadelphia, PA (US)

( * ) Notice: Subject to any disclaimer, the term of this patent is extended or adjusted under 35 U.S.C. 154(b) by 90 days.

(21) Appl. No.: 10/468,219

(22) PCT Filed: Mar. 1, 2002

(86) PCT No.: PCT/US02/06338

§ 371 (c)(1),
(2), (4) Date: Feb. 16, 2004

(87) PCT Pub. No.: WO02/071032

PCT Pub. Date: Sep. 12, 2002

(65) Prior Publication Data

US 2005/0025213 A1  Feb. 3, 2005

Related U.S. Application Data

(60) Provisional application No. 60/272,970, filed on Mar. 2, 2001.

(51) Int. Cl.
*G01M 3/04* (2006.01)
*G01N 25/72* (2006.01)

(52) U.S. Cl. .............................. 73/41; 374/4

(58) Field of Classification Search ................... 73/40, 73/41, 45, 45.4; 219/653; 374/5
See application file for complete search history.

(56) References Cited

U.S. PATENT DOCUMENTS

| | | | |
|---|---|---|---|
| 2,915,895 A | 12/1959 | Neiss | |
| 3,229,513 A | 1/1966 | Roberts | |
| 3,945,245 A | 3/1976 | Stehle et al. | |
| 4,220,839 A | 9/1980 | De Leon | |
| 4,319,111 A * | 3/1982 | Ishibashi | 219/653 |
| 4,517,827 A | 5/1985 | Tapscott | |
| 4,785,147 A | 11/1988 | Mucha et al. | |
| 4,878,379 A | 11/1989 | Deer | |
| 5,821,504 A * | 10/1998 | Sprenger et al. | 219/635 |

OTHER PUBLICATIONS

Guidance for Industry, Contain Closure Systems for Packaging Human Drugs and Biologics, Chemistry, Manufacturing, and Controls Documentation, U.S. Department of Health and Human Services Food and Drug Administrations, CDER, CBER, May 31, 1999, pp. 18-19.

* cited by examiner

*Primary Examiner*—Charles Garber
(74) *Attorney, Agent, or Firm*—Robert J. Smith

(57) ABSTRACT

A method and apparatus for heat stress testing medicament aerosol inhalation devices, such as a metered dose inhaler, is described. An electrical induction work coil is used to heat the inhalers to 55° C.±5° C. Heated inhalers are subsequently weighed to detect and reject nonconforming inhalers where a nonconforming amount of propellant has leaked.

21 Claims, 2 Drawing Sheets

METHOD AND APPARATUS TO STRESS TEST MEDICAMENT INHALATION AEROSOL DEVICE BY INDUCTIVE HEATING

This application is filed pursuant to 35 U.S.C. § 371 as a United States National Phase Application of International Patent Application Ser. No. PCT/US02/06338 filed Mar. 1, 2002, which claims priority from United States Provisional Application No. 60/272,970 filed on Mar. 2, 2001.

FIELD OF THE INVENTION

The present invention generally relates to the field of medicament inhalation devices, specifically metered dose inhalers, and to heat stress testing of such inhalation devices to detect and reject nonconforming inhalers.

BACKGROUND OF THE INVENTION

In the art of manufacturing medicament aerosol inhalation devices, recent attention has been aimed at detecting and rejecting potential and actual nonconforming devices. For example, a small percentage of aerosol inhalation devices leak or will leak due to manufacturing defects, such as broken or torn gaskets, loss of proper sealing, defective valve, swollen gasket(s), etc. Such defects cause a loss of aerosol propellant, which adversely affects or otherwise alters the performance of the inhalation device.

Recently, the Food and Drug Administration ("FDA") has become very concerned with leaking (or otherwise nonconforming or defective) aerosol inhalation devices, particularly MDI's. The performance of an MDI can be significantly altered when the propellant leaks, particularly where the propellant leaks in significantly amounts or at a significant rate. For example, a "gross leaker" may not deliver the medicament at all to the patient. MDI's that leak at more than an insignificant rate may under deliver the medicament. In other words, the medicament delivery from a leaking MDI does not conform to the dosing regimen set forth and approved by the FDA. In that case, the patient may not even realize that the insufficient medicament is being delivered to the lungs.

As a result, the FDA has begun requiring manufacturers to stress test aerosol inhalation devices and subsequently weigh the stressed devices to detect actual and potential nonconforming devices. Leaking MDI's will weigh less than what they are supposed to weigh. Stressed MDI's that lose a predetermined amount of propellant are rejected as nonconforming. The FDA has set conforming standards. The FDA has also set a temperature standard of 55° C.±5° C. for heat stress testing the MDI's.

Many methods and apparatus are available for heating MDI's. The present invention involves using electromagnetic induction heating to heat the electro-conductive materials present in the MDI, such as primarily the aluminum canister. Electromagnetic induction is a method of henerating heat within a metal part. Any electrical conductor can be heated by electromagnetic induction. As alternating current from the generator flows through the inductor, or work coil, a highly concentrated, rapidly alternating magnetic field is established within the coil. The magnetic field thus induces an electric potential in the part to be heated. The part represents a closed circuit. The induced voltage causes current to flow within the part. Eddy currents are typically established. The resistance of the part to the flow of the induced current causes heating.

The pattern of heating obtained by induction is determined by a number of factors: the shape of the induction coil producing the magnetic field, the number of turns in the coil, the operating frequency, the alternating current power input, and the nature of the work pieces. The rate of heating obtained by the coils depends on the strength of the magnetic field to which the part is exposed. In the work piece, this becomes a function of the induced currents and the resistance to electrical flow.

The depth of current penetration depends upon work piece permeability, resistivity, and the alternating current frequency. Since the first two factors vary comparatively little, the greatest variable is frequency. Depth of current penetration decreases as frequency increases. High frequency current is generally used when shallow heating is desired. Intermediate and low frequencies are used in applications requiring deeper heating.

The induction coil and associated components and the processes thereof of the present invention are advantageous. The present invention advantageously heats and stress tests MDI's in a relatively short period of time (i.e., dwell time), which permits in-line processing at high throughput. The present invention also advantageously employs a few relatively simple processing and material handling equipment resulting in low investment, reduced maintenance, high efficiency, and reliability. The present invention is further advantageous in that only the electroconductive portions of the MDI are heated significantly reducing the heating of plastic components (e.g., gaskets and valve components) that are susceptible to being unnecessarily damaged by heat. Still further, the present invention advantageously heat stress tests the MDI's without exposing the MDI's to steam or moisture (except any negligible moisture associated with the sealed heat exchangers) which can ingress into the MDI reducing product performance. Further benefits and advantages of the present invention are set forth herein.

SUMMARY OF THE INVENTION

One aspect of the invention is an apparatus for heating medicinal inhalation devices. The apparatus includes an electrical power supply and one or more induction coils. Preferably, the apparatus further includes a microprocessor for controlling the power supply in the range of 100–130 amps, preferably 110–115 amps, and more preferably about 113 amps, to heat the inhalation devices to a temperature in the range of 50–60° C., preferably around 55° C. By "about" or the like language as used herein, it is meant to include those values surrounding the recited value or range of values that achieve substantially the same desired ultimate result. The apparatus also preferably further includes a cooling system including a condenser and a pump, wherein a liquid coolant is pumped through the induction coil.

Preferably, the power supply provides up to 20 kilowatts (kW) at a frequency in the range of 240–440 kHz. A voltage of 140 volts may be applied to the induction coils. The electrical power supply may be operated in the range of 80–90% efficiency, preferably about 85%. The induction coil may be constructed from copper tubing and silver soldered joints.

Preferably, the induction coil is a single, continuous coil in the shape of a loop having two bridges, one at each end of the loop, respectively. The bridges are suitably sized and configured to directly heat each entire inhalation device. In other words, the bridges of the induction coil may be 4 inches in height for heating metered dose inhalers ("MDI's") that are 2–3 inches in height. Examples of MDI's that may be stress tested by this invention include those disclosed in U.S. Pat. Nos. 6,170,717; 6,131,566; 6,143,277; and 6,149,892, which are incorporated herein by reference.

Another aspect of the invention is an apparatus including the electrical powers supply and induction coil(s) described herein above, a conveyor, and a gating assembly for indexing a predetermined number of medicinal inhalation devices along the conveyor between the bridges of the induction coil. Preferably, the gating assembly further includes two heat exchangers suitably adapted and positioned to heat the first and last metered dose inhaler cycled and indexed within the induction coil. The heat exchanger may include an aluminum canister (similar to the canister used in the MDI's) adapted to be cooled by circulating cooling water.

Preferably, the gating assembly is adapted and controlled to index 32 metered dose inhalers per heating cycle. The MDI's are indexed one slug at a time where each slug may include 8 MDI's. Each heating cycle may include 4 slugs of 8 metered dose inhalers per slug. The heating cycle time may be in the range of 30–40 seconds. As such, the conveyor may have a line speed in the range of 100–140 metered dose inhalers per minute. An infrared thermometer may also be employed to measure the temperature of the metered dose inhalers. Preferably, the measured temperatures are fed to the microprocessor, whereby the microprocessor adjusts the power supply to heat the metered dose inhalers to the desired temperature, for example 55° C.±5° C. A check weighing device is also preferably employed to check the weight of the heated metered dose inhalers. Any nonconforming and/or leaking (e.g., gross leakers) MDI's are detected and summarily rejected/discarded.

Another aspect of the invention is a process or method of heat stress testing medicinal inhalation devices to detect and reject nonconforming or leaking devices. In general, the process includes providing one or more inhalation devices, and induction heating the one or more inhalation devices. Preferably, the inhalation devices are metered dose inhalers, whereby the metered dose inhalers are provided continuously (e.g., continuous runs) at a line speed in the range of 100–140 inhalers per minute.

Preferably, the process also includes indexing the continuously provided metered dose inhalers. The metered dose inhalers may be indexed in slugs of 8 providing 32 metered dose inhalers per induction heating cycle. During the heating cycle, the metered dose inhalers are preferably heated to a temperature in the range of about 50–60° C., preferably about 55° C. The temperature of the metered dose inhalers, the indexing, the induction heating, and other steps in the process may be computer process controlled by a microprocessor and other suitable electronic (e.g., sensors) and electromechanical equipment and instruments (e.g., pneumatic actuators).

The process preferably also includes the steps of check weighing the heated metered dose inhalers, and rejecting any nonconforming or leaking metered dose inhalers.

DETAILED DESCRIPTION OF THE PREFERRED EMBODIMENTS

Figure 1:
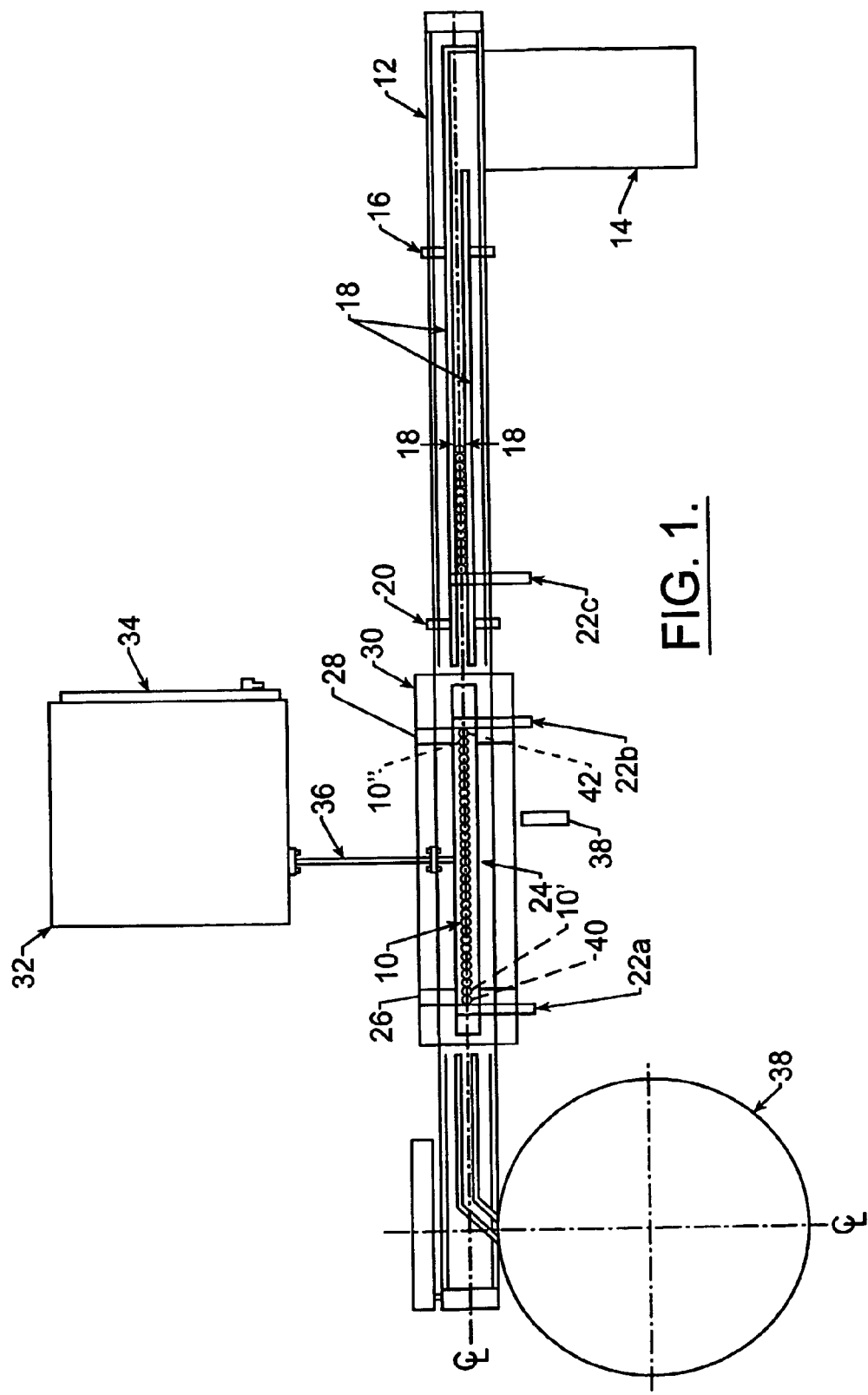
FIG. 1 is a top view of one aspect of the present invention.

Shown in FIG. 1 is a top view of various aspects of the invention. A plurality of medicament inhalation aerosol devices 10, such as MDI's, are conveyed along a conveyor 12. The MDI's 10 are loaded onto the conveyor 12 from a tray unloading station 14. From there, the MDI's 10 pass along the conveyor 12 past a backup cue sensor 16 to between rails 18. A can count sensor 20 keeps track of the number of MDI's 10 passing that point on the conveyor 12.

A computer-controlled gating assembly 22a,22b,22c indexes a predetermined number of MDI's 10 (called a slug, e.g., 8 MDI's per slug) into a zone above a channel portion 24 of the induction coil and between the end bridge portions 26,28 of the induction coil. Preferably, the induction coil is a continuous loop, single tube, single turn, channel/radiused type induction coil fabricated from copper tubing and silver soldered joints, such as those available from Pillar Industries of Brookfield, Wis. The coil 24,26,28 is water cooled using a chiller (not shown), and is pressure rated for 100 psi. Preferably, the channel 24 is about 4 feet long and the coil has a 0.75 inch face width to accommodate various MDI 10 sizes and configurations.

One of gating assembly levers 22c accumulates the MDI's 10 prior to entering the induction zone, and the other gating assembly levers 22a,22b are preferably pneumatically actuated during the induction heating cycle. The MDI's 10 can be alternatively indexed using a feedscrew or starwheel assembly. Preferably, 4 slugs of 8 MDI's 10 are indexed into the induction heating zone per heating cycle, thus having 32 MDI's heated per cycle. Preferably, the dwell time of the MDI's 10 in the heating induction cycle is around 9 seconds for 32 MDI's. A single slug of 8 MDI's may be indexed in 5 seconds. The heated MDI's 10 may be removed from the induction zone in around 3 seconds. Thus, line speeds of around 120 or greater MDI's per minute are preferably achieved. The gating assembly desirably allows the conveyor to run at a constant line speed.

The number of MDI's in each heat induction cycle affects the heating efficiency. In general, coil efficiency is improved by increasing the number of MDI's. In general, MDI's heat faster in a static mode, so the indexing method is more effective than where the MDI's are moving. A safety enclosure 30 constructed from LEXAN® is also preferably provided.

A controlled electrical power supply 32 having a control panel 34 supplies electrical power to the bus bar 36 which, in turn, supplies power to the induction coil 24,26,28. Preferably, the power supply 32 is a 20 kW, 400 kHz solid state RF generator, such as those available from Pillar Industries, MK-20, Model 7500. After completion of the heating cycle, the gating assembly 22a,22b releases the MDI's 10 conveying the MDI's 10 along the conveyor 12 to the accumulation table 38. A check weighing device (not shown) may be employed prior to or after the accumulation table 38 to detect and reject nonconforming (e.g., marginal sealing, defective valve, poor crimp, cut gasket, faulty component, etc.) or otherwise leaking (e.g., gross leaker) MDI's 10.

Preferably, the power supply 32 has a built-in timer that can be set according to the time necessary to heat a predetermined number of MDI's to a desired temperature or temperature range. For example, it may take 4 second to induction heat 32 MDI's 10 to 54–60° C.

The weight may be checked in-line or offline. A suitable check-weighing device is available from Anritsu. An infrared thermometer 38 may be used to measure the temperature of the MDI's 10 to ensure proper heating. Such measurements may be fed to the computer controlled power supply 32 to control heating. An irreversible temperature indicator may also be used by putting the test strip inside the MDI 10 and removing it after the heating cycle to determine the maximum temperature reached in the MDI. The infrared thermometer (Model OS91) and temperature test strips (Model U-08068-22) are available from Cole-Parmer.

Figure 2:
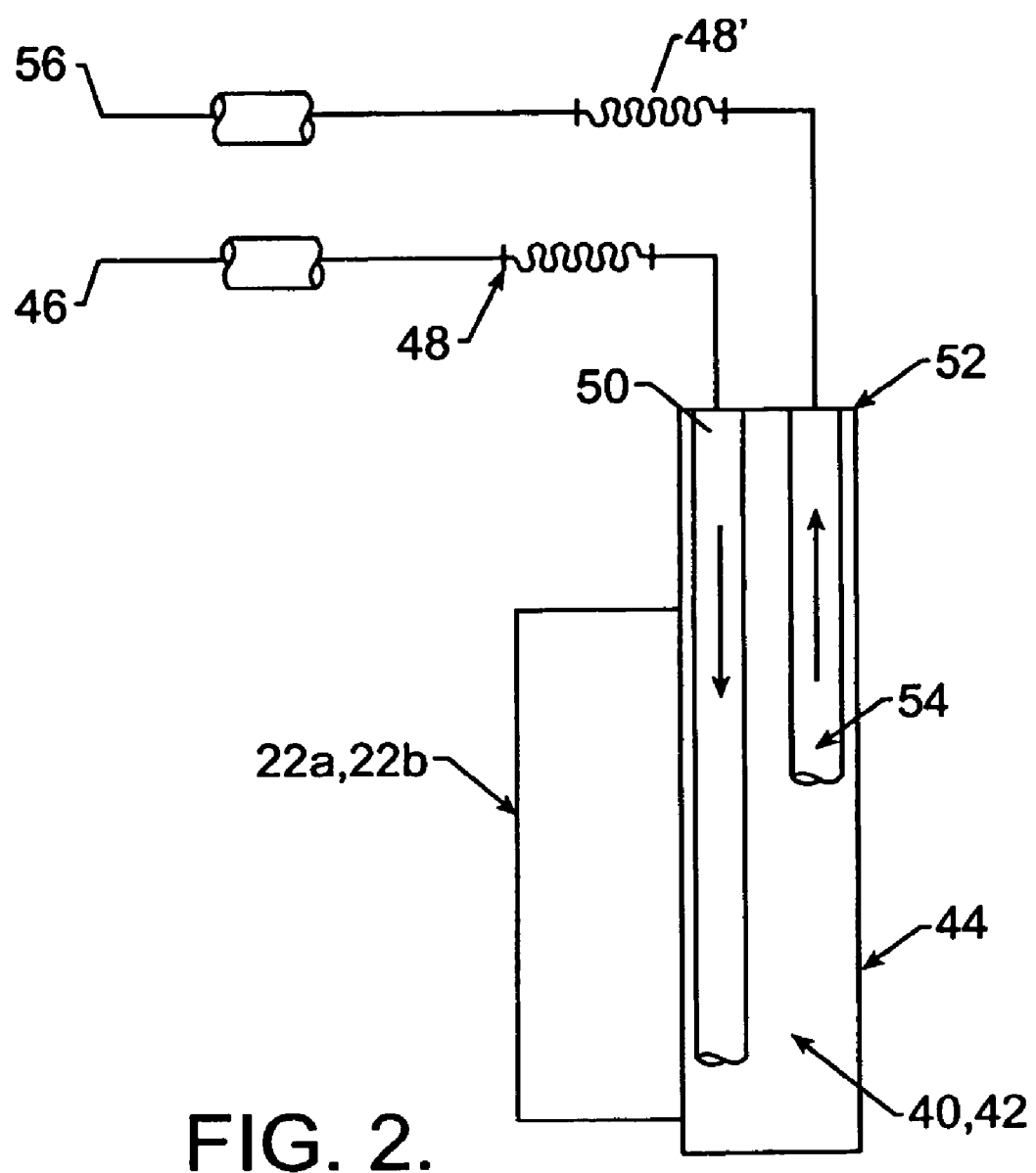
FIG. 2 is a side view of a portion of the gating assembly and heat exchanger of the present invention.

Shown in FIG. 2 is a preferred embodiment of the outer canister heat exchangers 40,42 of the present invention. The heat exchangers 40,42 are fixedly or removably attached to the non-conductive, placement arm of the gating assembly 22a,22b. The heat exchangers 40,42 include a sealed, aluminum canister 44 similar or identical in construction to the aluminum canister employed in the MDI's 10. The internal geometry of the heat exchangers is preferably designed for turbulent flow therein. A liquid, preferably water, is supplied to the heat exchangers 40,42 from a supply feed line 46 (from a chiller which is not shown) to a non-conductive, flexible line 48 to an internal supply tube 50 fixedly or removably attached to the removable canister lid 52. The lid 52 is removable to inspect, clean, or repair the interior of the heat exchanger 40,42. An internal return tube 54 is similarly fixedly or removably attached to the lid 52. Cooling water is returned to the chiller (not shown) through a cooling return line 56 that also includes a nonconductive, flexible line 48'.

In a linear configuration of objects, it is known in the art that induction heating efficiency is improved where each conductive object is proximate (preferably touching) to other conductive objects. This phenomenon is known as an electromagnetic effect inherent in induction heating. Thus, in this case, the first and last MDI's 10',10" are proximate to only one other MDI 10 whereas the other MDI's 10 are proximate to two other MDI's. It was determined that this electromagnetic effect reduced the induction heating efficiency of the first and last MDI's 10',10" such that they were 5° C. cooler. This would be problematic since the FDA has required stress testing of all MDI's in the range of 55° C.±5° C.

The present invention overcomes this potential problem. The heat exchangers 40,42 are preferably employed to straddle the first and last MDI's 10',10" (preferably 32 total MDI's) so that they are positioned proximate (touching or close) to the first and last MDI's during the heating cycle. During the induction heating cycle, the first and last MDI's 10',10" are heated sufficiently the same as the other MDI's because each MDI 10',10" is proximate to another conductive MDI 10 and a respective canister 44 of each respective heat exchanger 40,42. The heat exchangers 40,42 are continuously or intermittently cooled with cooling water to control their temperature. Cooling is needed so that a more than insignificant amount of heat is not transferred to the first and last MDI 10',10" by conductive and/or convection. Such non-induction forms of heat transfer may occur without cooling because the heat exchangers 40,42 are repetitively heated whereas the MDI's 10, 10',10" should be heated by induction only once.

I claim:

1. An apparatus for heating medicinal inhalation devices comprising:
    an electrical power supply, and
    one or more induction coils, wherein the induction coil is a single, continuous coil in the shape of a loop having first and second bridges on first and second ends of the loop, respectively, and wherein the first and second bridges are suitable sized and configured to directly heat each entire inhalation device;
    a conveyor; and
    a computer-controlled gating assembly for indexing a predetermined number of medicinal inhalation devices along the conveyor between the first and second bridges of the induction coil, wherein the medicinal inhalation devices are metered dose inhalers.

2. The apparatus according to claim 1, further including a microprocessor for controlling the power supply in the range of 100–130 amps to heat the inhalation devices to a temperature in the range of 50–60° C.

3. The apparatus according to claim 2, further including a cooling system comprising a condenser and a pump, wherein a liquid coolant is pumped through the induction coil, and wherein the electrical power supply has a maximum power output of 20 kilowatts and operates in the range of 80–90% efficiency.

4. The apparatus according to claim 2, wherein the power supply provides up to 20 kilowatts and 50–450 kHz, and wherein 140 volts is applied to the one or more induction coils.

5. The apparatus according to claim 2, wherein the induction coil is constructed from copper tubing and silver soldered joints.

6. The apparatus of claim 1, wherein the gating assembly further includes first and second heat exchangers suitably adapted and positioned to heat a first and last metered dose inhaler indexed within the one or more induction coils.

7. The apparatus of claim 6, wherein the first and second heat exchanger each comprise an aluminum canister adapted to be cooled.

8. The apparatus of claim 1, wherein the gating assembly is adapted to index 32 metered dose inhalers per heating cycle, wherein 4 slugs of 8 metered dose inhalers per slug are indexed each cycle, and wherein the cycle time is in the range of 30–40 seconds.

9. The apparatus of claim 1, wherein the conveyor has a line speed in the range of 100–140 metered dose inhalers per minute.

10. The apparatus of claim 1 further including an infrared thermometer to measure the temperature of the metered dose inhalers.

11. The apparatus of claim 10, wherein the measured temperatures are fed to the microprocessor, and wherein the microprocessor adjusts the power supply to heat the metered dose inhalers to a temperature of about 55° C.

12. The apparatus of claim 1 further including a weighing device to check the weight of the heated metered dose inhalers.

13. An apparatus for heating medicinal inhalation devices comprising:
    an electrical power supply means,
    one or more induction coil means, wherein the induction coil means is a single, continuous coil in the shape of a loop having first and second bridges on first and second ends of the loop, respectively, and wherein the first and second bridges are suitable sized and configured to directly heat each entire inhalation device;
    conveying means; and
    a computer-controlled gating means for indexing a predetermined number of medicinal inhalation devices along the conveying means between the first and second bridges of the induction coil means, wherein the medicinal inhalation devices are metered dose inhalers.

14. A process of heat stress testing medicinal inhalation devices to detect and reject nonconforming or leaking devices comprising the acts of:
    providing a plurality of inhalation devices, wherein the plurality of inhalation devices are metered dose inhalers provided continuously;
    indexing the continuously provided metered dose inhalers; and induction heating the plurality of inhalation devices.

15. The process of claim 14, wherein the metered dose inhalers are provided continuously at a line speed in the range of 100–140 inhalers per minute.

16. The process of claim 15, wherein the metered dose inhalers are heated to a temperature in the range of 50–60° C.

17. The process of claim 16 wherein the metered dose inhalers are heated to a temperature of about 55° C.

18. The process of claim 17, wherein the temperature of the metered dose inhalers, the indexing and the induction heating is computer process controlled.

19. The process of claim 14, wherein the metered dose inhalers are indexed in slugs of 8 providing 32 metered dose inhalers per induction heating cycle.

20. The process of claim 14 further including the acts of:
check weighing the heated metered dose inhalers, and
rejecting any nonconforming or leaking metered dose inhalers.

21. A process of heat stress testing medicinal inhalation devices to detect and reject nonconforming or leaking devices comprising the steps of:
providing a plurality of inhalation devices, wherein the plurality of inhalation devices are metered dose inhalers provided continuously;
indexing the continuously provided metered dose inhalers; and
induction heating the plurality of inhalation devices.

* * * * *